United States Patent [19]

DuFault

[11] Patent Number: 4,799,486
[45] Date of Patent: Jan. 24, 1989

[54] REFRACTORILESS ATRIAL SENSING IN DUAL CHAMBER PACEMAKERS

[75] Inventor: Robert A. DuFault, Roseville, Minn.
[73] Assignee: Cardiac Pacemakers, Inc., St. Paul, Minn.
[21] Appl. No.: 25,571
[22] Filed: Mar. 13, 1987
[51] Int. Cl.⁴ .................... A61N 1/00; H05G 00/00
[52] U.S. Cl. .................................... 128/419 PG
[58] Field of Search ......... 128/696, 704, 705, 419 PG

[56] References Cited

U.S. PATENT DOCUMENTS

| | | | |
|---|---|---|---|
| 4,537,200 | 8/1985 | Widrow | 128/696 |
| 4,543,963 | 10/1985 | Gessman | 128/419 PG |
| 4,557,266 | 12/1985 | Schober | 128/419 PG |

Primary Examiner—Francis Jaworski
Assistant Examiner—George Manuel
Attorney, Agent, or Firm—Orrin M. Haugen; Thomas J. Nikolai; Frederick W. Niebuhr

[57] ABSTRACT

A method and apparatus for suppressing the ventricular component from an atrial sensing lead used with a dual chamber cardiac pacer, thus obviating the need for an atrial sense refractory period to prevent oversensing of the ventricular interference. The invention utilizes an adaptive filter embodying the Widrow-Hoff least mean square (LMS) algorithm which is connected to receive signals from an endocardial lead having a bipolar ventricular electrode and a unipolar atrial electrode. The bipolar electrodes disposed in the ventricle are connected as the "input" $X_k$ signal to the LMS adaptive filter while the unipolar atrial electrode output is connected as the "desired" or reference signal $d_k$. In accordance with the LMS algorithm, the "error" signal is fed back and used to adjust the tap weights of the adaptive linear filter until the output thereof closely approximates the "desired" signal and then the "error" signal becomes a good approximation of the atrial signal alone, without the ventricular depolarization signal.

5 Claims, 1 Drawing Sheet

REFRACTORILESS ATRIAL SENSING IN DUAL CHAMBER PACEMAKERS

BACKGROUND OF THE INVENTION

I. Field of the Invention:

This invention relates generally to sensing circuitry for use in a dual chamber demand pacemaker, and more particularly to a method and apparatus for obviating the need for an atrial refractory period following the occurrence of ventricular depolarization by effectively reducing to an inconsequential level the R-wave contribution to the signal on the atrial sensing lead.

II. Discussion of the Prior Art:

So-called dual chamber pacemakers have been devised which closely emulate the electrical activity of the heart. In such pacemakers, means are provided for sensing both atrial and ventricular depolarization signals and for generating pacing signals for both the ventricles and the atrium. In that the energy content of the QRS complex occurring during depolarization of the ventricles is significantly higher than that of the P-wave signal, the R-wave or the ventricular pacing spike often appear as a contaminant on the atrial sensing lead. Oversensing of the QRS on the atrial pacemaker lead has been common throughout the history of pacing and, in this regard, reference is made to a publication by Goldman, et al, entitled "Permanent Transvenous Atrial Pacing" which appeared in volume 21, page 138 of the Canadian Journal of Surgery (1978) and to an editorial authored by Furman entitled "Electrical Magnetic Interference" published in Pace in 1982. While atrial bipolar leads tend to minimize oversensing by minimizing the far field QRS spacial gradient propagated to the atrium through the use of closely spaced electrodes in the atrium, nonetheless, in practically all prior art dual chamber pacers, an atrial sense refractory blanking period, under control of the ventricular/sense pace circuitry, must be employed. Such oversensing is even more of a problem when unipolar atrial leads are used in that the major portion of the QRS gradient falls between the atrial tip electrode and the indifferent plate consisting of the can of the pulse generator.

Because the atrial QRS field and the P-wave have somewhat similar amplitude and spectral distributions, it is quite difficult to separate the two by traditional linear filtering means. In a dual chamber pacemaker operating in the DDD mode, oversensing is generally dealt with by incorporating a refractory interval following a ventricular beat or pacing spike in which the atrial sense applifier is inhibited. This renders the atrial sense amplifier inactive for a significant portion of the cardiac cycle. Because, in many instances of DDD implantation, the A/V interval is dependent upon the pacer device, there can be no inherent physiologic guarantee that the P-wave will maintain any fixed temporal relationship to the QRS, or to any other inherent mark or event. Thus, the imposition of a long atrial refractory period will increase the probability of undersensing atrial activity.

It is the principal purpose of the present invention to provide a signal processing technique permitting linear sensing of the P-wave throughout the entire cardiac cycle, while diminishing or substantially eliminating QRS oversensing by suppressing the QRS residue appearing on the atrial lead of a dual chamber pacer.

Another object of the invention is to provide a method and apparatus for use in a dual chamber pacer whereby oversensing of the QRS complex on the atrial pacemaker lead is obviated without resorting to the imposition of a refractory period.

SUMMARY OF THE INVENTION

In accordance with the present invention, an endocardial pacing lead having a ventricular tip electrode and a ring surface electrode, also located in the ventricle, and a unipolar atrial lead, having a tip electrode in the right atrium and a remotely located indifferent electrode, are appropriately coupled to an adaptive filter of the Least Means Square (LMS) variety of the type described in "Adaptive Signal Processing" by B. Widrow and S. Stearns, Prentice-Hall, Inc. The signals picked by the atrial electrodes are applied as the "desired" signal while the bipolar ventricular electrodes provide the "input" signal. The ventricular lead signal is dominated by the ventricular equivalent dipole near field while the atrial signal comprises near and far field atrial activity and the ventricular far field signal. Stated more directly, signals due to ventricular activity are superimposed on the atrial lead along with the Pwave signal. The LMS adaptive filter then undertakes to approximate the "desired" signal, i.e., the ventricular component on the atrial head, by adjusting the tap weights or coefficients on the adaptive linear filter until its output (the "estimate" signal) closely approximates the "desired" signal. The "estimate" is then subtracted from the "desired", cancelling the QRS contribution. When this condition obtains, the "error" signal becomes a good approximation to the atrial signal alone without the ventricular component.

As pointed out in my co-pending application, Ser. No. 025,731, entitled "Dual Channel P-Wave Detection in Surface Electrocardiographs" and application Ser. No. 025,811, entitled "Dual Channel Coherent Fibrillation Detection System", filed on even date herewith, the LMS algorithm can be implemented by appropriately programming a microprocessor and that teaching is hereby incorporated by reference.

Further objects and advantages of the invention will become apparent to those skilled in the art from the following detailed description of a preferred embodiment, especially when considered in conjunction with the accompanying drawings.

DESCRIPTION OF THE PREFERRED EMBODIMENT

Figure 1:
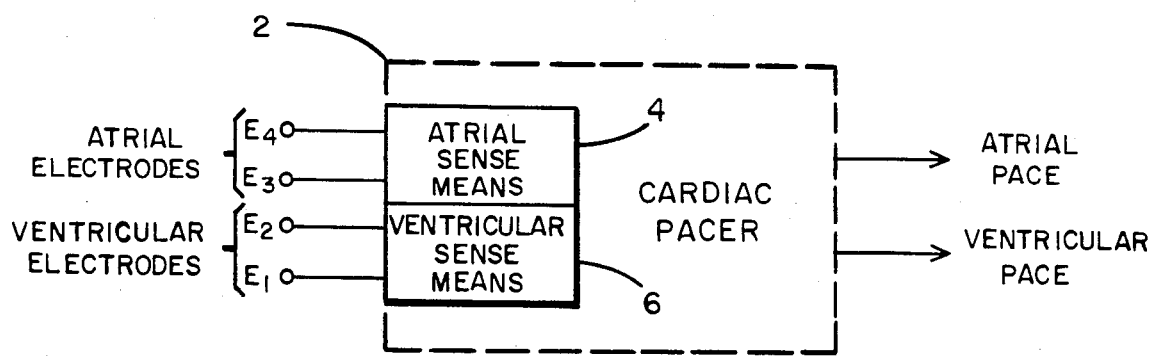
FIG. 1 is a block diagram of a dual chamber pacer in which the present invention finds use.

Referring first to FIG. 1, there is shown by means of a general block diagram a dual chamber cardiac pacer 2 in which the present invention finds application. As those skilled in the art recognize, a dual chamber pacer is capable of sensing atrial depolarization signals (P-waves) and ventricular depolarization signals (R-waves) and are operative to selectively deliver stimulating pulses to either or both the atrium and the ventricle to maintain A-V synchrony. As is pointed out in the Markowitz U.S. Pat. No. 4,343,311, the atrial sense amplifier in such a dual chamber pacemaker is intended to respond only to P-waves of the electrocardiogram, but that R-waves may be sensed by the atrial sense applifier. Because this oversensing initiates the AV delay interval, which is followed by the pacemaker issuing a ventricular electrical stimulation pulse, this latter pulse may fall into the socalled "vulnerable period". It is known that pacing into the "vulnerable period" can induce fibrillation.

Attempts have been made to discriminate the P-wave from the R-wave using electrical linear bandpass filtering techniques, but such attempts have not been successful because of the significant overlap in the frequency and time domain of each.

In accordance with the present invention, the cardiac pacer 2 includes an atrial sense means 4 in the form of an adaptive filter which is capable of suppressing R-waves. More particularly, and with reference to FIG. 2, numeral 10 identifies a schematic representation of the heart where the left and right ventricles and the left and right atria are identified by the legends LV, RV, LA and RA, respectively. Positioned in the heart is a multi-electrode lead set 12 having a ventricular tip electrode $E_1$ and a proximally positioned ring surface electrode $E_2$, both positioned within the right ventricle. The electrodes $E_1$ and $E_2$ comprise a bipolar pair and are coupled by conductors in the lead set 12 to the inputs of a first differential amplifier 14. The lead set 12 also includes a unipolar tip electrode $E_3$ shown as being disposed in the right atrim (RA) and that electrode is also coupled by a conductor in the lead set to a first input of a second differential amplifier 16. The second input to differential amplifier 16 comes from the indifferent electrode $E_4$ which may be a second electrode positioned in the atrium to form a bipolar pair, or which may be the metal can containing the circuitry of the present invention as well as the other electronics comprising an otherwise conventional dual chamber pacer or the like. In that the present invention is directed to the apparatus and method for recovering P-waves from an atrial lead that may also include QRS artifacts superimposed thereon, the disclosure of the circuitry comprising the conventional dual chamber pacemaker with which the apparatus of the present invention may be used is not deemed to be necessary for complete understanding of the present invention. In this regard, reference may be had to the Schober U.S. Pat. No. 4,388,927 which describes a dual channel pacer having fairly complex circuitry for determining the occurrence of atrial depolarization while discriminating against ventricular activity. The present invention would allow a more facile form of P-wave detection and obviates the need for an atrial refractory period following the occurrence of a natural or paced ventricular contraction.

To permit linear sensing of the P-wave even when adjacent to or concurrent with the QRS, while simultaneously diminishing or eliminating QRS oversensing by specific suppression of the QRS residue on the atrial lead, the output from differential amplifier 14 is applied as the "input" signal $X_k$ to the adaptive LMS filter module 18. This signal, in that it is derived from the bipolar electrodes $E_1$ and $E_2$ located in the right ventricle, will predominately carry the QRS signal. Any P-wave artifacts may be safely ignored in this instance. The signal appearing at the output of the differential amplifier 16 will be due substantially to atrial depolarization, but will also incorporate a ventricular component picked up differentially by the atrial sensing electrodes $E_3$, $E_4$. This, then, becomes the "desired" signal $d_k$, using the nomenclature set out in the aforementioned book by B. Widrow and S. Stearns. As is more fully explained in my aforereferenced co-pending patent application entitled, "Dual Channel Coherent Fibrillation Detection System", the content of which is hereby incorporated by reference, there is described another application of the LMS algorithm, and in that application, the method of implementing the algorithm using a digital computer is set out. That copending application also defines various terms and parameters, again following those of Widrow and Stearns, supra, which are also used herein. As is set out in the abovereferenced materials, there are numerous ways of estimating the transfer function between linearly and causally related processes, but the LMS algorithm is deemed well-suited to the present application in terms of its ease and simplicity of implementation, the speed as measured by the number of computations needed to achieve real-time rates at a given bandwidth, stability and convergence rate. In that in the suppression of R-wave activity on an atrial lead permits a sufficiently long convergence time, instability does not become a problem, making the LMS algorithm well suited.

Again, following the development of Widrow and Stearns, it can be seen that the input signal vector $X_k$ (k being a time index) is convolved with a weight vector $W_k$ (indicating that weights adapt over time) to form an output signal $\hat{d}_k$ which is an "estimate" of the value of the reference signal $d_k$ emanating from the differential amplifier 16 at the time, k. An error signal, $\epsilon_k = d_k - \hat{d}_k$ is then produced at the summing node 20 which is the difference between the desired signal and its estimate.

In vector notation, $$\epsilon_k = d_k - X_k^T W_k$$

Following the calculation of $d_k$ and $\epsilon_k$, the weight vector is updated to $W_{k+1}$ by execution of the update algorithm where:

$$W_{k+1} = W_k + 2 \mu \epsilon_k X_k$$

where $\mu$ is the adaptation time constant.

Figure 2:
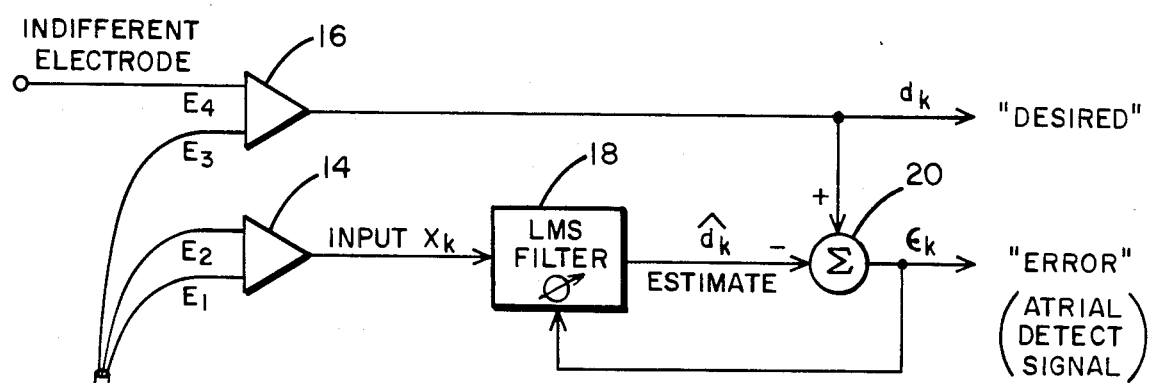
FIG. 2 is a schematic block diagram illustrating the principles of the present invention.

It can be seen, then, that the LMS filter depicted in FIG. 2 functions to approximate the desired signal, $d_k$ by adjusting the coefficience of the adaptive linear filter until the output, $\hat{d}_k$, closely approximates $d_k$. When this occurs, the error signal, $\epsilon_k$, is minimized in its ventricular component and comprises a good approximation of the atrial (P-wave) signal alone without the ventricular R-wave component superimposed thereon. The memory time span of the adaptive filter is generally restricted to encompass only the QRS complex so that the subsequent P-wave pulse will not be cancelled along with the unwanted R-wave.

Figure 3:
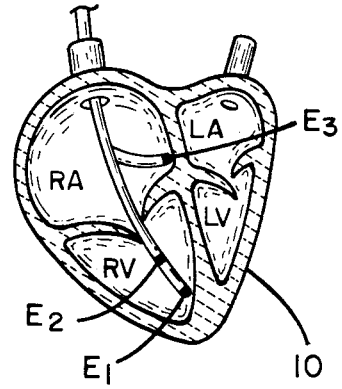
FIG. 3 illustrates by means of a series of waveforms aligned along the time axis the signals present at various identified points in the block diagram of FIG. 1, once convergence of the LMS filter has taken place.
Figure 3:
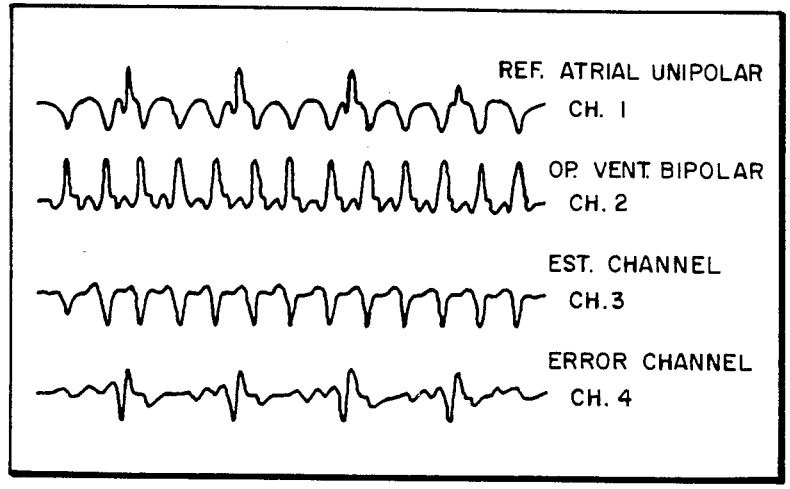

FIG. 3 is a series of waveforms illustrating the applicability of the present invention to signals collected during a human study, the upper waveform labeled channel 1 depicts the desired signal $d_k$ emanating from the differential amplifier 16 while the waveform on the line below it, labeled channel 2, comprises the "input" signal, $X_k$, emanating from the differential amplifier 14. The waveform labeled ch. 3 is the waveform observed at the output of the LMS filter 18 and is the "estimate" signal, $\hat{d}_k$. Finally, the lowermost waveform, channel 4, is the signal present on the error channel following convergence of the adaptive filter 18. Comparing the waveforms on channels 1 and 4, it can readily observed that the P-wave components remain of a significant magnitude or energy whereas the QRS component, which had been present and picked up by the electrode $E_3$ is suppressed to the point where it can be readily discriminated against by merely utilizing a comparator with a fixed voltage reference set above the QRS noise level on the error channel.

The present invention has been found to effectively operate to suppress the ventricular contribution on an atrial lead without altering the basic morphology of the atrial signal. In that it operates to suppress the ventricular component to the point where it can be readily discriminated, it becomes unnecessary to provide for an atrial sense refractory period following the occurrence of a QRS complex.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself. In particular, those skilled in the art will realize that the invention can not only be practiced using a programmed digital computer, but also can be implemented using special purpose digital logic devices (hardware).

What is claimed is:

1. In a dual chamber cardiac pacer of the type having first electrode means disposed in the ventricle of the heart for detecting ventricular depolarization signals and second electrode means disposed in the atrium of the heart for primarily detecting atrial depolarization signals, atrial sensing means responsive to the signals on said second electrode means for suppressing those signals on said second electrode means due to said ventricular depolarizing signals comprising:
    (a) an adaptive filter coupled to said first electrode means for receiving as an input signal said ventricular depolarizing signal;
    (b) a summing circuit coupled to the output of said adaptive filter and to said second electrode means, said summing circuit producing an error signal proportional to the difference between the output of said adaptive filter and the signals on said second electrode means; and
    (c) means coupling said error signal to said adaptive filter for continuously varying the parameters of said adaptive filter whereby said filter converges to the point where said error signal is minimized.

2. The dual chamber pacer as in claim 1 wherein said adaptive filter is a least means square (LMS) adaptive filter.

3. The dual chamber pacer as in claim 1 wherein said error signal indicates the occurrence of P-waves.

4. The dual chamber pacer as in claim 1 wherein said atrial sensing means remains operative throughout the entire cardiac cycle.

5. A method of operating a dual chamber pacemaker of the type including ventricular pacing means, ventricular sensing means and atrial sensing means such that natural or artificial electrical activity originating in the ventricle is not oversensed by said atrial sensing means, comprising the steps of:
    (a) positioning a first electrode in the ventricle of the heart, said first electrode being coupled to said ventricular sensing means;
    (b) positioning a second electrode in the atrium of the heart, said second electrode being coupled to said atrial sensing means;
    (c) connecting the input of an LMS adaptive filter means to said ventricular sensing means;
    (d) summing the output of said LMS adaptive filter means with the output from said atrial sensing means for generating an error signal proportional to the difference between said output of said LMS adaptive filter and the output of said atrial sensing means; and
    (e) applying said error signal to said LMS filter for continuously adjusting the parameters of said LMS adaptive filter until said error signal is minimized.

* * * * *